United States Patent [19]

Mertes et al.

[11] 4,060,517

[45] Nov. 29, 1977

[54] CONTINUOUS MANUFACTURE OF POLYAMIDES

[75] Inventors: Friedrich Mertes, Ludwigshafen; Helmut Doerfel, Heidelberg; Eduard Heil, Limburgerhof; Claus Cordes, Weisenheim, all of Germany

[73] Assignee: BASF Aktiengesellschaft, Ludwigshafen, Germany

[21] Appl. No.: 559,255

[22] Filed: Mar. 17, 1975

[30] Foreign Application Priority Data

Apr. 8, 1974 Germany .............................. 2417003

[51] Int. Cl.$^2$ ............................................. C08G 69/04
[52] U.S. Cl. ................................ 260/78 R; 260/78 A; 260/78 L; 526/65
[58] Field of Search .................. 260/78 R, 78 A, 78 L

[56] References Cited

U.S. PATENT DOCUMENTS 3,185,672  5/1965  Clemo et al. ...................... 260/78 R Primary Examiner—Harold D. Anderson
Attorney, Agent, or Firm—Keil, Thompson & Shurtleff

[57] ABSTRACT

An improved process for the continuous manufacture of polyamides by continuously conveying the aqueous solution of a salt of essentially equivalent amounts of a diamine, or of a mixture of several diamines, and of a dicarboxylic acid, or of a mixture of several dicarboxylic acids, or of mixtures of such salts with lactams and/or aminocarboxylic acids, through several reaction zones under polyamide-forming conditions, wherein the mixture of starting materials is heated, in a first reaction zone, to from 200° to 300° C, preferably from 220° to 280° C, at pressures which are above the corresponding saturation vapor pressure of water and prevent the formation of a vapor phase, the pressure action on the polycondensation mixture is released in a second reaction zone and condensation of the mixture, to form high molecular weight polyamides, is then completed in further reaction stages. According to the invention, a. the mixture of starting materials is heated, in the first reaction zone, until the polycondensation conversion is at least 80% and preferably 90%, b. in the second zone the pressure acting on the polycondensation mixture is released, adiabatically, to levels of not less than 3 atmospheres, preferably not less than 5 atmospheres, and not more than 20 atmospheres, preferably not more than 15 atmospheres, so as to reach temperatures below 215° C, preferably 210° C, c. the polycondensation mixture is then heated in a third reaction zone, comprising a heat exchanger consisting of heat exchange elements connected in parallel, to from 220° to 330° C, preferably from 250° to 300° C, in the course of less than 5 minutes and preferably less than 1 minute, the heating being carried out preferably in the presence of the water vapor formed during the adiabatic release of the pressure (in stage b), with application of heat and evaporation of the bulk of the water, at the pressure level to which the pressure has previously been released or at a lower pressure, and d. in further reaction stages, the condensation is completed, under the conditions prevailing at the end of the third reaction zone and, finally, by conventional methods, to form high molecular weight polyamides.

3 Claims, 1 Drawing Figure

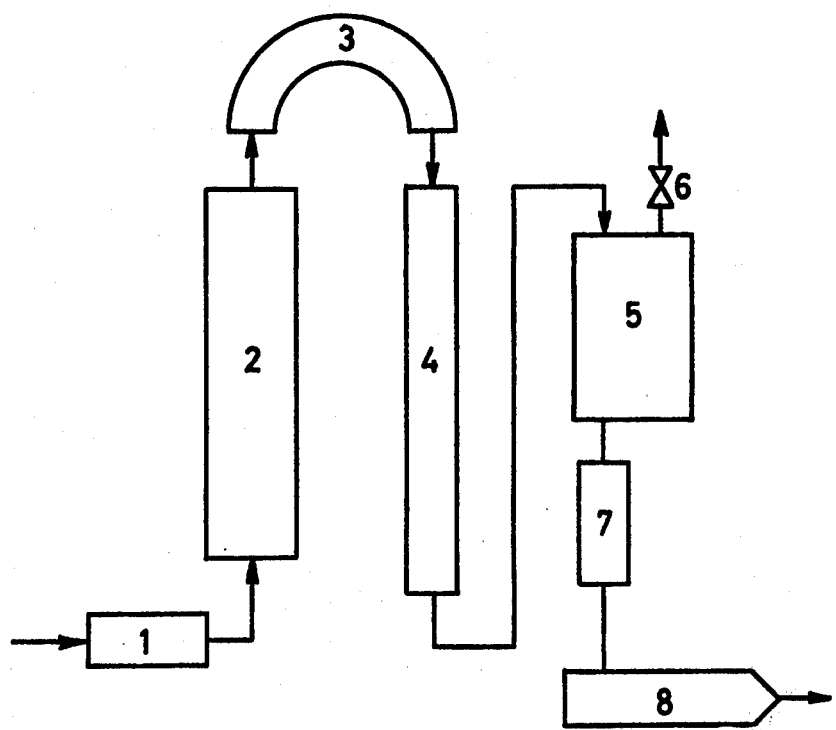

CONTINUOUS MANUFACTURE OF POLYAMIDES

The present invention relates to an improved process for the continuous manufacture of polyamides by continuously conveying the aqueous solution of a salt of essentially equivalent amounts of a diamine, or of a mixture of several diamines, and of a dicarboxylic acid, or of a mixture of several dicarboxylic acids, or of mixtures of such salts with lactams and/or aminocarboxylic acids.

Several processes of this nature have already been disclosed. Thus, according to the process of German Pat. No. 916,589, the polyamide-forming starting materials are conveyed through pairs of stages in which the polycondensation is carried out under pressure in the first stage and under reduced pressure in the second stage. Several such pairs of stages are arranged in series, as required. The process is relatively complicated and entails heavy expenditure for equipment. To terminate the stages carried out at various pressures and generate superatmospheric pressures, feed pumps are used and in order that these should function perfectly it is necessary to separate the vapor phase from the polycondensate after each pair of stages. The polycondensation, and the heating of the polycondensate, are carried out in one and the same heat exchanger, which must have a very large volume if the polycondensation is to be effective. The heat is transferred from the wall of the heat exchanger to the liquid phase of the polycondensate and therefore requires large heat exchange surfaces. Water is only evaporated adiabatically in this process and when manufacturing nylon from a 60% strength solution of hexamethylenediamine adipate a large number of adiabatic pressure release stages arranged in series becomes necessary because evaporation of as little as 10% of water lowers the temperature by about 80° C.

U.S. Pat. No. 2,361,717 discloses a process for the continuous manufacture of, in particular, nylon wherein the aqueous solution of hexamethylenediamine adipate is initially precondensed, at 183° C and 82 atmospheres gage pressure in the first reaction zone of a laboratory apparatus which is heated very intensely from all sides by being immersed in a heating bath at from 280° to 290° C; the reaction mixture is then simultaneously heated and brought to a lower pressure, with evaporation of water, by passing it through a throttle value and a heated pipe coil in which the pressure is reduced, and is then once again brought to a lower pressure and subjected to a final condensation in a screw-type apparatus not described in any detail. In this process, the pressure reduction, and evaporation of water, take place at the same time as heat is applied. The lowest temperature reached after passing the pressure release value is stated to be 240° C, corresponding to a water vapor pressure of 33 atmospheres.

The fact that in U.S. Pat. No. 2,361,717 the pressure release is carried out semi-adiabetically and semi-isothermally is presented as a disadvantage in a large number of subsequent publications. These recommend measures by means of which the pressure is to be released as isothermally as possible. Attampts are made to do this by, e.g., isothermal evaporation of the water under constant pressure from the pre-condensation reactor, prior to the actual pressure release stage. Other processes use heat exchangers in which there is a high pressure drop, such as very long pipes of which the cross-section increases in stages, so as to spread the pressure drop and the associated cooling of the polycondensate over the entire length of the heat exchanger and compensate for the cooling by intense application of heat. Other processes dispense with indirect heat exchange and heat the polycondensate, which has been subjected to adiabatic pressure release, immediately after the pressure release by direct heating through mixing it with a polycondensate which has already been brought to a lower pressure and has been heated, so as to avoid the undesired cooling and crystallization of the polymer.

According to the disclosures of British Pat. No. 674,954 (col. 2, pages 6 et seq.), the disadvantages of the process of U.S. Pat. No. 2,361,717 are that at high throughputs the polycondensate is supercooled as a result of the pressure reduction being too abrupt, and that an inhomogeneous end product is formed. According to the process of the above British patent, these difficulties are circumvented by distilling the bulk of the water present isothermally and under constant pressure from the precondensation reactor during the precondensation and reducing the pressure acting on the substantially dehydrated precondensate by using a long heated pipe of which the cross-section increases stepwise. This method achieves a continuous pressure reduction and gradual evaporation, coupled with adequate heat supply. The disadvantage of this process is that when distilling off water during the precondensation, some of the more volatile diamine is also distilled off and during the subsequent condensation the amounts of dicarboxylic acid and diamine present are no longer equivalent to one another. A further problem is the scaling-up of the process to industrial scale. For each size of installation, the pressure-release pipe which gives optimum results must be determined experimentally and designed accordingly.

British Pat. No. 924,630 describes the continuous polycondensation of aqueous hexamethylenediamine adipate in a single stage in a long pipe of which the cross-section increases stepwise. This method also requires expensive experiments, to establish the size of the pressure-release pipe for each size of installation, when scaling up to an industrial scale. A futher disadvantage is that the vessel which follows the pie, and in which the nylon which has condensed out and is therefore heat-sensitive is separated from the water vapor, is insufficiently self-purging.

Inter alia, the following solutions have also been proposed for the critical stage of releasing the pressure, and evaporating water from the precondensate, in the course of the continuous manufacture of polyamides from diamines and dicarboxylic acids:

German printed application No. 1,162,562 describes releasing the pressure acting on the nylon precondensate by passing the precondensate through a throttle valve and a capillary into a polycondensate which has already been brought to a lower pressure and been heated. The disadvantage of this process is, inter alia, that when scaled up to an industrial scale a very large number of capillaries must be arranged in parallel.

According to the process of German Pat. No. 1,131,011, a nylon precondensate which has been preconcentrated is mixed, in a circulatory system, with about a ten-fold amount of polycondensate which has been brought to normal pressure and been heated. This process also suffers from the disadvantage of uncoltrolled distillation of diamine during the precondensation. Furthermore, the mechanism for releasing the pressure is complicated.

According to the process of German printed application No. 1,158,257, nylon precondensate is released into a heated vessel through a ball valve. This is intended to spray the polymer in the form of fine droplets and to evaporate the water, whilst avoiding the formation of a solid product, through rapid contact of the finely divided polymer with the very hot wall of the vessel. The disadvantage of this process is that its scaling up to an industrial scale presents difficulties.

It may thus be concluded from the state of the art that there is a marked prejudice against adiabatic release of pressure in the continuous manufacture of polyamides and that therefore all endeavors should be directed toward conducting this pressure release as isothermally as possible.

Contrary to the opinion of those skilled in the art, the above disadvantages of the earlier processes are avoided if the process of the present invention is followed, using a substantially adiabatic pressure-release stage. The process of the present invention is based on a process for the continuous manufacture of polyamides by continuously conveying the aqueous solution of polyamide-forming constituents through several reaction zones under polyamide-forming conditions, wherein the mixture of starting materials is heated, in a first reaction zone, to from 200° to 300° C, preferably from 220° to 280° C, at pressures which are above the corresponding saturation vapor pressure of water and prevent the formation of a vapor phase, the pressure acting on the polycondensation mixture is released in a second reaction zone and condensation of the mixture, to form high molecular weight polyamides, is then completed in further reaction stages. In the process according to the invention a. the mixture of starting materials is heated, in the first reaction zone, until the polycondensation conversion is at least 80% and preferably 90%, b. In the second zone the pressure acting on the polycondensation mixture is released adiabatically to levels of not less than 3 atmospheres, preferably not less than 5 atmospheres, and not more than 20 atmospheres, preferably not more than 15 atmospheres, so as to reach temperatures below 215° C, preferably 210° C, c. the polycondensation mixture is then heated in a third reaction zone comprising a heat exchanger consisting of heat exchange elements connected in parallel, to form 220° to 330° C, preferably from 250° to 300° C, in the course of less than 5 minutes and preferably less than one minute, the heating being carried out preferably in the presence of the water vapor formed during the adiabatic release of the pressure (in stage b), with application of heat and evaporation of the bulk of the water, at the pressure level to which the pressure had previously been released or at a lower pressure, and d. in further reaction stages, the condensation is completed, under the conditions prevailing at the end of the third reaction zone and, finally, by conventional methods, to form high molecular weight polyamides.

Aqueous solutions of polyamide-forming constituents which may be used are aqueous solutions of a salt of substantially equivalent amounts of a diamine, or for a mixture of several diamines, and of a dicarboxylic acid, or of a mixture of several dicarboxylic acids, or mixtures of these salts with lactams and/or aminocarboxylic acids.

The process according to the invention can in particular be used for the continuous manufacture of nylon, starting from aqueous solutions of hexamethylenediamine adipate, and related similarly high-melting and heat-sensitive polyamides. The conditions to be maintained in the first reaction zone depend on the nature of the starting materials which are to be polycondensed. Suitable conditions for the manufacture of conventional polyamides have proved to be temperatures of from 220° to 330° C, preferably from 230° to 280° C, pressures above the saturation vapor pressure of water, and polycondensation times of from 10 to 360 minutes, preferably from 20 to 120 minutes. According to a particularly preferred embodiment of the process the polycondensate which has passed through the third reaction zone is heated in a fourth reaction zone under the conditions of the third reaction zone, but at temperatures which are from 2° to 20° C lower, for less than 45 minutes, preferably for from 10 to 30 minutes, and separated from the bulk of the water vapor formed, released adiabatically, in a fifth reaction zone, to pressures below 3 atmospheres gage or seven to subatmospheric pressure heated, in a sixth reaction zone, to from 250° to 300° C, with evaporation of further water, and post-condensed, in a last reaction zone, for from 15 to 60 minutes at from 260° to 300° C, preferably from 265° to 290° C.

According to another embodiment, the polycondensation mixture, together with all the water vapor formed, after passing through the third reaction zone, is brought adiabatically to atmospheric pressure or subatmospheric pressure by passage through a throttle valve and is then heated to from 250° to 300° C whilst evaporating water, separated from the water vapor and subjected to the final condensation.

Polyamides of lower melting point than nylon 66 can be manufactured advantageously by bringing the polycondensate to atmospheric or slightly increased pressure as early as in the second reaction zone, heating the polcondensate together with the adiabatically released water vapor in a heat exchanger, whilst evaporating water, separating it from the bulk of the water vapor and completing the condensation under atmospheric or subatmospheric pressure.

Preferably, a heat exchanger consisting of several heat exchange units connected in parallel, and in particular a tube bundle heat exchanger, is used to heat the polycondensate whilst at the same time evaporating the bulk of the water.

The post-condensation of the precondensate which has been brought to atmospheric or subatmospheric pressure is carried out, eg., in a self-purging twin screw reactor with forced feed. However, the post-condensation can also be carried out in a vessel, with or without stirring means, under slightly increased pressure or under subatmospheric pressure, or in a thin film evaporator or similar equipment.

The particular advantages of the process of the invention over batchwise processes are the short residence times during which the polycondensation mixture is kept above 250° C, whilst its advantages over conventional continuous processes are the simplicity of the equipment, the fact that all overheating is avoided, and, in particular, the easy adaptability of the equipment to any desired polycondensation throughput and to the particular conditions required for the manufacture of a variety of polyamides. The last-mentioned advantages result from the design of the equipment and the use of predominently conventional apparatus, the design of which for the various throughputs required can easily be calculated beforehand.

The manufacture of polyamides from aqueous solutions of salts of diamines and dicarboxylic acids requires a large amount of heat to evaporate the solvent water and the water of polycondensation. In the process of the invention, the heat is supplied to the polycondensate in a heterogeneous vapor/liquid phase. This permits bubbling evaporation and the achievable heat transition coefficients are several times greater than those achievable with heat transfer to a homogeneous liquid phase. The heat exchangers used can therefore be relatively small and can be of compact design because it is possible to arrange heat exchanger units in parallel.

The attached drawing sets forth a flow diagram illustrating a preferred embodiment of the subject process, the individual elements of the drawing being conventional.

The process according to the invention is carried out, eg., by pumping the aqueous solution of the salts of diamines and dicarboxylic acids, or the aqueous solutions of the starting materials for corresponding copolyamides, continuously, under pressure, from a stock vessel via a heat exchanger 1 into the precondensation reactor 2, which is completely filled with liquid and through which the material preferably flows upwards, to avoid forming gas cushions. The precondensation reactor 2 is operated, eg., at 280° C and 80 atmospheres gage, with residence times of 45 minutes. The precondensate, which has been polycondensed to the extent of more than 80%, is adiabatically released through a valve into a distributor tube 3 kept at from 10 to 20 atmospheres gage. Whilst being released, the precondensate and water vapor cool to from 180° to 210° C and then pass into a tube bundle evaporator 4 in which the bulk of the water is evaporated and at the same time the precondensate is heated to from 220° to 330° C, preferably from 250° to 300° C. After evaporation, the pressure settles to a value of from 8 to 15 atmospheres gage. In a downstream separating vessel 5, the water vapor escapes through an orifice at the top, via a pressure-regulated valve 6. The polymer melt collects in the lower part of the separating vessel 5 and remains there, eg., for 30 minutes at from 165° to 270° C. The walls of the separating vessel 5 are preferably kept at from 2° to 10° C below the temperature of the polycondensate which enters from the heat exchanger 4, to avoid the formation of vapor bubbles and foam in the separating vessel 5. The polycondensate is continuously released adiabatically through a second pressure-release valve in the bottom of the separating vessel 5 and is then heated in a subsequent heat exchanger 7, together with the water vapor formed, to from 270° to 290° C, passed into the post-condensation apparatus 8, separated therein from the water vapor, and post-condensed at from 270° to 290° C, under atmospheric pressure or subatmospheric pressure, using times of from 25 to 40 minutes.

Vertical elongated reaction vessels with a length to diameter ratio of 10:1 and an outlet at the highest point are particularly suitable for carrying out the reaction of the arting materials in the first reaction zone. The polycondensation mixture flows upward through the reaction vessel. This embodiment reliably prevents interference from the formation of gas cushions in the pre-condensation reactor; such gas cushions cause the formation of crusts and cracked products at the phase boundaries and result in uneven flow of the polycondensation mixture through the apparatus.

The precondensation is advantageously carried out by endeavoring to provide plug flow in the precondensation reactor. Back-mixing can be avoided by the use of packings, suitable inserts or permanent baffling.

The Examples which follow illustrate the invention.

EXAMPLE 1

A solution of 60 kg of the salt of adipic acid and hexamethylenediamine, 600 g of hexamethylenediamine and 40 kg of water is kept under autogenic pressure at 110° C in the absence of air. 10 kg/hour of this solution are continuously brought to 80 atmospheres pressure and pumped through a tube 1, 1 m long and of 25 mm diameter, which is heated to 290° C, whereby the solution is brought to 280° C. The polycondensation mixture then passes upward through a vertical pressure vessel 2 2 m long and of 70 mm internal diameter, in which the polycondensation mixture remains for an average of 45 minutes at 280° C and 80 atmospheres gage. It is then released, through an orifice at the highest point of the pressure vessel, via a pressure-regulated needle valve, into a pipe arc 3 which is heated to counteract heat losses and from there into a vertical tube 4 2.5 m long and of 25 mm diameter, which is heated to 290° C. As soon as the installation is in operation, the precautionary heating of the pipe arc can be switched off. Virtually regardless of the heating, the water vapor saturation temperature corresponding to the pressure to which the mixture is being released, in this case 180° C and 10 atmospheres gage, establishes itself in the pipe arc 3 without any interference with the polycondensation through premature solidification of nylon precondensate. In the downstream heat exchanger, which is heated to 290° C, the polycondensate which has been released adiabatically, and the water vapor, are heated to 275° C, with evaporation of the bulk of the water present, and the material then passes into an elongated separating vessel 5 of about 10 l capacity, the walls of which are kept at 270° C. Water vapor escapes through an orifice in the upper part of the separating vessel, via a pressure-regulated valve 6 which maintains the release pressure. The polymer melt remains in the lower part of the separating vessel 5 for 15 minutes and is then released, via a second pressure-release valve into a pipeline 17 which is heated to 290° C and is under atmospheric pressure, through which the material, together with the water vapor formed, is conveyed to a type ZSK 53 twin-screw extruder 8. The twin-screw extruder is 36 D long and contains about 1/3 feed units and ⅓ kneading units. In the intake zone, the water vapor which accompanies the polycondensate is separated off and escapes through a vent pipe. The polycondensate is conveyed through the twin-screw extruder at from 280° to 285° C and atmospheric pressure in the course of 20 minutes, during which little back-mixing occurs, and is extruded as a strand. This is granulated and dried, giving colorless polyamide granules of K value 71. The end product can be used, eg., to injection-mold articles having excellent mechanical proporties, or to spin filaments.

EXAMPLE 2

The process is carried out as in Example 1 except that 9 kg/hour of a 50% strength aqueous solution of the salt obtained from equivalent amounts of adipic acid and 2,2-di-(4-aminocyclohexyl)-propane are used. In addition, the process is modified in the following respects: the residence time of the precondensate in the separating vessel, in which the water vapor and polycondensate are separated, is restricted to a few minutes and the post-condensation in the twin-screw extruder is carried out at 50 mm Hg instead of atmospheric pressure. The end product is a glass-clear polyamide of K value 60, which has a melt viscosity of about 60,000 poise and can be injection-molded to give glass-clear articles. Because of the high melt viscosity of the end product it is not possible to manufacture the same polyamide by batchwise polycondensation in an autoclave; instead, only a relatively low molecular weight precondensate can be produced batchwise and has to be converted to an end product of sufficiently high molecular weight by heating in the solid state. This process is uneconomical compared to the continuous process and its second stage results in yellowing and oxidative degradation of the product because small traces of oxygen cannot be totally excluded from the granules being heated.

EXAMPLE 3

100 kg/hour of a 60% strength aqueous solution of the salt of adipic acid and hexamethylenediamine, with a 1 percent by weight excess of hexamethylenediamine, are heated to 280° C by means of a tube bundle heat exchanger which is itself heated to 290° C by means of a diphenyl/diphenyl oxide mixture, and are conveyed upward through a pressure tube 10 m long and of 90 mm diameter. The polycondensate is then released through a pressure regulated valve into a connecting tube which widens out and is in turn connected to a heat exchanger consisting of 6 tubes of 16 mm diameter, connected in parallel, The polycondensate and water vapor flow downward through the heat exchanger and in doing so are heated from 190° to 280° C. The polycondensate collects in a downstream separating vessel of about 70 l capacity. The water vapor exits at 9 atmospheres gage through an orifice in the upper part of the separating vessel, via a pressure-regulated release valve. The level of the polymer melt maintained in the reaction vessel is equivalent to about 12.5 l, corresponding to a residence time of the polymer of 15 minutes. The separating vessel is kept at 275° C. After having passed through the lower part of the separating vessel, the polycondensate is released to atmospheric pressure through a second valve and is heated to 280° C in a doenstream pipe coil itself heated to 290° C. The heated polycondensate and water vapor pass into a type ZDSR 130 reactor screw, where the post-condensation is carried out at from 280° to 185° C and under atmospheric pressure, the residence time being 30 minutes. The end product is extruded as strands, chilled with water, chopped off and dried. Colorless nylon granules of K value 72 are obtained; they may be converted to moldings or filaments having excellent properties.

We claim:

1. A process for the manufacture of a polyamide by continuously conveying the aqueous solution of a salt of essentially equivalent amounts of a diamine, or of a mixture of several diamines, and of a dicarboxylic acid, or of a mixture of several dicarboxylic acids, through several reaction zones under polyamide-forming conditions, wherein
   a. in a first reaction zone the mixture of starting materials is heated to a temperature of at least 220° C, but not higher than 300° C, at a pressure which is above the corresponding saturation vapor pressure of water and prevents the formation of a vapor phase, until the polycondensation conversion is at least 80%, but without completing the condensation in this zone,
   b. in a second reaction zone the pressure acting on the polycondensation mixture is released adiabatically to a level of not less than 3 atmospheres and not more than 20 atmospheres, so as to reach a temperature below 215° C,
   c. in a third reaction zone the polycondensation mixture is heated by means of a heat exchanger consisting of heat exchanger elements connected in parallel, to from 220° to 330° C, in the course of less than 5 minutes, with evaporation of the bulk of the water, at a pressure level not higher than the pressure to which the mixture had previously been expanded,
   d. in a fourth reaction zone the polycondensation mixture is separated from the water vapor, and
   e. finally the condensation is completed under the conditions prevailing at the end of the third reaction zone to form a high molecular weight filament-forming polyamide.

2. A process as claimed in claim 1, wherein, when using an aqueous solution of essentially equivalent amounts of hexamethylenediamine and adipic acid the polycondensation is taken to a conversion of 90% in the first reaction zone at from 220° to 250° C, in the second reaction zone the pressure is released adiabatically to bring the polycondensation mixture to from 180° to 200° C, and thereafter, in the third reaction zone, the polycondensation mixture, together with the water vapor formed during the adiabatic pressure release, is heated to from 260° to 290° C in a heat exchanger, the residence time in this zone being less than one minute.

3. A process as set forth in claim 1 wherein an aqueous solution of a salt of at least one diamine and at least one dicarboxylic acid is polymerized.

* * * * *